(12) United States Patent
Morales Sánchez et al.

(10) Patent No.: US 11,213,536 B2
(45) Date of Patent: Jan. 4, 2022

(54) ACYLATED COMPOUNDS FOR THE TREATMENT OF OCULAR PATHOLOGIES

(71) Applicants: CONSEJO SUPERIOR DE INVESTIGACIONES CIENTÍFICAS, Madrid (ES); FUNDACIÓN PÚBLICA ANDALUZA PROGRESO Y SALUD, Seville (ES)

(72) Inventors: Juan Carlos Morales Sánchez, Granada (ES); Pablo Peñalver Puente, Granada (ES); Francisco Javier Díaz Corrales, Seville (ES); María Lourdes Valdés Sánchez, Seville (ES); Ana Belén García Delgado, Seville (ES); Adoración Montero Sánchez, Seville (ES)

(73) Assignees: CONSEJO SUPERIOR DE INVESTIGACIONES CIENTIFICAS, Madrid (ES); FUNDACION PUBLICA ANDALUZA PROGRESO Y SALUD, Seville (ES)

( * ) Notice: Subject to any disclaimer, the term of this patent is extended or adjusted under 35 U.S.C. 154(b) by 0 days.

(21) Appl. No.: 16/463,786

(22) PCT Filed: Nov. 17, 2017

(86) PCT No.: PCT/ES2017/070760
§ 371 (c)(1),
(2) Date: May 23, 2019

(87) PCT Pub. No.: WO2018/096196
PCT Pub. Date: May 31, 2018

(65) Prior Publication Data
US 2019/0275068 A1 Sep. 12, 2019

(30) Foreign Application Priority Data

Nov. 23, 2016 (ES) ................ P 201631503

(51) Int. Cl.
| | | |
|---|---|---|
| *A61K 31/7034* | (2006.01) | |
| *A61P 27/02* | (2006.01) | |
| *A61K 47/40* | (2006.01) | |
| *A61K 31/7024* | (2006.01) | |

(52) U.S. Cl.
CPC ...... *A61K 31/7034* (2013.01); *A61K 31/7024* (2013.01); *A61K 47/40* (2013.01); *A61P 27/02* (2018.01)

(58) Field of Classification Search
None
See application file for complete search history.

(56) References Cited

U.S. PATENT DOCUMENTS

| | | |
|---|---|---|
| 6,414,037 B1 | 7/2002 | Pezzuto et al. |
| 6,573,299 B1 | 6/2003 | Petrus |
| 6,878,751 B1 | 4/2005 | Donnelly et al. |
| 2006/0035984 A1 | 2/2006 | Docherty |
| 2007/0014833 A1* | 1/2007 | Milburn ............ A61K 31/56 424/427 |
| 2009/0143376 A1* | 6/2009 | Milburn ............ A61P 21/00 514/233.2 |

FOREIGN PATENT DOCUMENTS

| | | | |
|---|---|---|---|
| CN | 105503970 A * | 4/2016 | ........ C07H 15/203 |
| EP | 2 087 894 A1 | 8/2009 | |
| EP | 2514426 A1 | 10/2012 | |
| ES | 2 362 035 A1 | 6/2011 | |
| ES | 2362065 A1 | 6/2011 | |
| ES | 2 393 746 T3 | 12/2012 | |
| WO | WO 00/12534 A2 | 3/2000 | |
| WO | WO-2007020673 A1 * | 2/2007 | ........ A61K 31/7028 |

OTHER PUBLICATIONS

International Search Report and Written Opinion received in PCT Application No. PCT/ES2017/070760, dated Apr. 2, 2018.
Falomir et al., "Cytotoxic, Antiangiogenic and Antitelomerase Activity of Glucosyl- and Acyl-Resveratrol Prodrugs and Resveratrol Sulfate Metabolites", Chembiochem, vol. 17, No. 14, 2016, pp. 1343-1348.
Larrosa et al., "Preventive Oral Treatment with Resveratrol Pro-prodrugs Drastically Reduce Colon Inflammation in Rodents", J of Med Chem, vol. 53, No. 20, 2010, pp. 7365-7376.
Wang et al.,"Highly efficient enzymatic synthesis of novel polydatin prodrugs with potential anticancer activity", Process Biochemistry 2017, vol. 52, Jan. 2017, pp. 209-213.
Supplementary Extended Search Report issued in EP patent application No. EP17875009.7, dated May 27, 2020.
King, Robert E., et al. "Resveratrol reduces oxidation and proliferation of human retinal pigment epithelial cells via extracellular signal-regulated kinase inhibition." Chemico-biological interactions 151.2 (2005): 143-149.
Garcia-Delgado et al., "Rasagiline delays retinal degeneration in a mouse model of retinitis pigmentosa via modulation of Bax/Bcl-2 expression", CNS Neurosci Ther. (2018), 00:1-8.
Wang et al., "Light-induced Nrf2$^{-/-}$ mice as atrophic age-related macular degeneration model and treatment with nanoceria laden injectable hydrogel", Scientific Reports (2019), 9: 14573.

* cited by examiner

*Primary Examiner* — Dale R Miller
(74) *Attorney, Agent, or Firm* — Knobbe, Martens, Olson & Bear, LLP (57) ABSTRACT

The present invention relates to the therapeutic use of acylated piceid derivative compounds in ocular pathologies, in particular retinitis pigmentosa and in age-related macular degeneration.

6 Claims, 9 Drawing Sheets

ACYLATED COMPOUNDS FOR THE TREATMENT OF OCULAR PATHOLOGIES

CROSS REFERENCE TO RELATED APPLICATIONS

This application is the U.S. National Phase under 35 U.S.C. § 371 of International Application No. PCT/ES2017/070760 filed Nov. 17, 2017, designating the U.S. and published as WO 2018/096196 on May 31, 2018, which claims the benefit of Spanish Application No. P 201631503, filed Nov. 23, 2016.

The present invention relates to the therapeutic use of acylated piceid derivatives in ocular pathologies, particularly in retinal degeneration. The present invention can therefore be encompassed within the field of pharmaceuticals.

PRIOR ART

Retinitis pigmentosa (RP) and age-related macular degeneration (AMD) are a cause of blindness in the adult population due to the degeneration of photoreceptors and of the retinal pigment epithelium (RPE). RP is a rare disease, but the prevalence of AMD is quite high, estimated at 8-16% of the population between 50 and 64 years of age. Like for RP, no treatment exists for the dry variety of AMD despite its high prevalence.

Patent application WO 2007020673 A1 discloses compounds derived from glycosylated hydroxystilbenes that might be useful for the treatment of some ocular diseases. Acylated piceid (3-glucosyl resveratrol) derivatives have been proposed for the treatment of inflammatory bowel diseases (ES 2362065 A1) and as antibiotics (Selma M V et al., *J. Agric. Food. Chem.* 2012, 60(30), 7367-74).

Nevertheless, there are currently no effective treatments that can prevent or slow down the degenerative process of photoreceptors or RPA in dry AMD or RP. Therefore, it would be beneficial to search for new molecules that are useful for the treatment or prevention of these and other ocular diseases involving retinal degeneration.

DESCRIPTION OF THE INVENTION

The present invention provides compounds that are useful for the manufacture of a pharmaceutical composition for the treatment or prevention of ocular diseases. To this end, it is demonstrated in the examples how some acylated derivatives of resveratrol induce the protection of the photoreceptors in two animal models of retinal degeneration.

In a first aspect, the present invention relates to the use of compounds of the general formula (I)

(I)

or any of its isomers, or any of its salts, preferably any pharmaceutically acceptable salt, esters, tautomers, polymorphs, pharmaceutically acceptable hydrates, or prodrugs, derivatives, solvates, or the like, or any combination thereof, where:

$R_1$ is a $C_1$-$C_{22}$ alkyl group or a $C_2$-$C_{22}$ alkenyl group, with $R_1$ preferably being a $C_1$-$C_{22}$ alkyl group;

for the preparation of a pharmaceutical composition for the prevention and/or treatment of ocular pathologies.

In a preferred embodiment, $R_1$ is a $C_2$-$C_{20}$ alkyl group, more preferably a $C_3$-$C_{17}$ alkyl group.

In the present invention, the term "alkyl" refers to aliphatic, linear, or branched chains having from 1 to 22 carbon atoms, e.g., methyl, ethyl, n-propyl, i-propyl, n-butyl, tert-butyl, sec-butyl, n-pentyl, n-hexyl, etc. The alkyl group preferably has between 2 and 20 carbon atoms, and more preferably between 3 and 17 carbon atoms.

In the present invention, the term "alkenyl" refers to unsaturated, linear, or branched aliphatic chains having from 2 to 22 carbon atoms and having between one and six unsaturations depending on the number of carbons, for example, without limitation to vinyl, allyl, oleyl, linoleyl, linolenyl, eicosapentaenoyl, docosahexaenoyl, etc.

In a preferred embodiment, the compounds of the invention can be selected from among:

1 trans-resveratrol-3-O-(6'-O-butanoyl)-β-D-glucopyranoside (1),

2 trans-resveratrol-3-O-(6'-O-octanoyl)-β-D-glucopyranoside (2), trans-resveratrol-3-O-(6'-O-hexadecanoyl)-β-D-glucopyranoside (3), trans-resveratrol-3-O-(6'-O-octadecanoyl)-β-D-glucopyranoside (4), and any combination thereof.

The pharmaceutical composition of the present invention can be formulated for administration in a variety of manners that are known in the art. Examples of preparations include any solid composition (tablets, pills, capsules, granules, etc.) or liquid composition (solutions, suspensions, or emulsions) for oral, topical, or parenteral administration. The composition of the present invention can also be in the form of sustained-release drug formulations or any other conventional delivery system, and can thus be contained, without limitation thereto, in nanoparticles, liposomes, or nanospheres, in a polymeric material, in a biodegradable or non-biodegradable implant, or in biodegradable microparticles such as biodegradable microspheres, for example.

Such a composition and/or its formulations can be administered to an animal, including a mammal and hence to a human, in a variety of manners, including but not limited to intraperitoneal, intravenous, intradermal, intraspinal, intrastromal, intraarticular, intrasynovial, intrathecal, intralesional, intraarterial, intramuscular, intranasal, intracranial, subcutaneous, intraorbital (sub-retinal, intravitreal), intracapsular, topical, or percutaneous administration, or by means of transdermal patches, nasal spray, surgical implant, internal surgical painting, or infusion pump.

In an embodiment that is even more preferred, the composition of the invention is formulated for ophthalmic administration. The expression "formulated for ophthalmic administration" refers to a formulation that enables the composition of the invention to be administered ocularly—including, but without limitation thereto, topically or intraocularly—without such administration adversely affecting the properties, e.g., optical and/or physiological properties, of the eye.

Examples of the composition of the invention that are formulated for ophthalmic administration include but are not limited to said composition in combination with water, salts, a polymeric liquid or semi-solid vehicle, a phosphate buffer, or any other ophthalmically acceptable liquid vehicle thereof that is known in the art.

In a preferred embodiment, the pharmaceutical composition of the invention comprises a system for the controlled release of the compounds of the invention; more preferably, they comprise cyclodextrins and even more preferably 2-hydroxypropyl beta-cyclodextrin.

Therefore, another aspect of the present invention relates to an ophthalmological composition comprising at least one compound of the formula (I) as described above together with a controlled-release system, particularly a cyclodextrin, and more specifically 2-hydroxypropyl beta-cyclodextrin.

In another aspect, the present invention relates to a method for treating and/or preventing ocular pathology in a mammal, preferably a human, comprising the administration of a therapeutically effective amount of a composition of the general formula (I) as described above.

The dosage for obtaining a therapeutically effective amount depends on a variety of factors, such as the age, weight, sex, or tolerance of the individual to whom the composition of the invention is to be administered, for example. In the meaning used in this description, the term "therapeutically effective amount" refers to the amount of the composition (I) calculated to produce the desired effect and, in general, will be determined inter alia by the characteristics of the composition, the age, condition, and history of the patient, the severity of the alteration or disorder, and the route and frequency of administration.

The ocular pathologies of the present invention can be selected from among:

1. Hereditary degenerative pathologies of the retina, including retinitis pigmentosa and all those pathologies within the group of retinal dystrophies which include, but are not limited to: autosomal dominant retinitis pigmentosa, autosomal recessive retinitis pigmentosa, retinitis pigmentosa linked to the X chromosome, sporadic retinitis pigmentosa, retinitis pigmentosa associated with other syndromes, Cokayne syndrome, cone dystrophies, cone and rod degeneration, Leber's congenital amaurosis, retinitis punctata albescens, choroideremia, choroidal and retinal gyrate atrophy, choroidal generalized dystrophy, juvenile retinoschisis, Wagner's vitreoretinal degeneration, autosomal dominant vitreoretinal choroidopathy, fundus albipunctatus, Stargardt's disease, Best vitelliform macular dystrophy, Usher syndrome, Bardet-Biedl syndrome, fenestrated macular dystrophy, Sorsby pseudoinflammatory macular dystrophy, dominant drusen, among other retinal dystrophies involving degeneration of photoreceptors and/or EPR.

2. Early- and/or late-onset age-related (wet or neovascular) and/or non-exudative (dry or atrophic) macular degeneration; as well as other macular diseases such as: epiretinal membrane, macular hole, and macular edema, etc.

3. Degenerative inflammatory pathologies of the retina and the optic nerve of infectious, immune, vascular, traumatic, post-surgical, or teratogenic origin such as: ocular toxoplasmosis, cryptococcosis, lupus, Behcet's disease, diabetic retinopathy, ischemic optic neuropathy, optic neuritis, detachment of the retina, vitrectomy, internal limiting membrane peeling, surgery, retinoblastoma, etc.

4. Ocular pathologies that increase intraocular pressure and that involve degeneration of the ganglion cells of the retina and atrophy of the optic nerve such as: open-angle or closed-angle glaucoma.

5. Neurological pathologies that are accompanied by degenerative lesions of the retinal or optic nerve such as: amyotrophic lateral sclerosis, multiple sclerosis, Parkinson's disease, Alzheimer's disease, Graefe syndrome, Hallgren syndrome, Hallen Vorden Spatz syndrome, autosomal dominant cerebellar ataxia, and pigmentary degeneration of the retina.

6. Other ocular pathologies that occur with inflammation of the cornea, choroid, ciliary body of any etiology such as: uveitis, scleritis, keratoconjunctivitis, corneal transplant surgery, cataract surgery.

7. Other ocular or neurodegenerative pathologies that involve infiltration of microglia or shortening of telomeres due to cellular aging or oxidative stress.

In one preferred embodiment, the ocular pathologies are selected from among retinitis pigmentosa and age-related macular degeneration.

Throughout the description and the claims, the expression "comprises" and variants thereof are not intended to exclude other technical features, additives, components, or steps. For those skilled in the art, other objects, advantages, and features of the invention will be apparent in part from the description and in part from the practicing of the invention. The following examples and figures are provided for the sake of illustration and are not intended to limit the scope of the present invention.

DESCRIPTION OF THE FIGURES

FIG. 11. Fundus and autofluorescence of the retina in normal mice (WT control), untreated Prpf31$^{A216P/+}$ mice (KI control), and Prpf31$^{A216P/+}$ mice treated with eye drops administered daily for two and a half months containing 2 mM resveratrol (KI RES) or 2 mM compound 2 diluted in a 13% hydroxypropyl-beta-cyclodextrin vehicle in PBS (KI 2) or only with the 13% hydroxypropyl-beta-cyclodextrin vehicle in PBS (KI CYCLE). Both WT and KI mice that did not receive any treatment (WT control and KI control) were used as controls. All the groups were subjected to 5,000 lux for 3 h and the evaluations were made 15 days after inducing light damage, the eye drops having been continued during this 2-week period. In the KI control, KI CYCLE, and KI RES groups, areas with autofluorescent punctiform yellowwhite lesions (arrows) were observed which can be seen clearly in the enlargement of the image in the lower row. Moreover, areas of focal atrophy (arrowheads) were observed in these mice. Fundi with this type of characteristic were considered abnormal. In the majority of the fundi of the WT control and KI 2 groups, this type of lesion was not observed, and these fundi were classified as normal.

FIG. 12. Thickness of the retina quantified by means of OCT in normal mice (WT control), untreated Prpf31$^{A216P/+}$ mice (KI control), and Prpf31$^{A216P/+}$ mice treated with eye drops administered daily for two and a half months containing 2 mM resveratrol (KI RES) or 2 mM compound 2 diluted in a 13% hydroxypropyl-beta-cyclodextrin vehicle in PBS (KI 2) or only with the 13% hydroxypropyl-beta-cyclodextrin vehicle in PBS (KI CYCLE). Both WT and KI mice that did not receive any treatment (WT control and KI control) were used as controls. All the groups were subjected to 5,000 lux for 3 h and the evaluations were made 15 days after inducing light damage, the eye drops having been continued during this 2-week period. The retinal maps (A) show the thickness of the retina in 9 concentric areas at 1, 2.22, and 3.45 mm and represented by a colorimetric scale (B). The data were quantified and are shown in (C). The bars represent averages of retinal thickness measured in μm+/−the standard error (WT control n=5, rest of the groups n=10). The normality of the data was confirmed by the Kolmogorov-Smirnov test (P=0.98); to determine differences in the means of the groups, one-way ANOVA (P<0.001) and post hoc LSD tests were performed. *P<0.001 KI control vs. KI RES or KI control vs KI 2.

FIG. 13. Evaluation of the amplitude of the c-wave in normal mice (WT control), untreated Prpf31$^{A216P/+}$ mice (KI control), and Prpf31$^{A216P/+}$ mice treated with eye drops administered daily for two and a half months containing 2 mM resveratrol (KI RES) or 2 mM compound 2 diluted in a 13% hydroxypropyl-beta-cyclodextrin vehicle in PBS (KI 2) or only with the 13% hydroxypropyl-beta-cyclodextrin vehicle in PBS (KI CYCLE). Both WT and KI mice that did not receive any treatment (WT control and KI control) were used as controls. All the groups were subjected to 5,000 lux for 3 h and the evaluations were made 15 days after inducing light damage, the eye drops having been continued during this 2-week period. The amplitude of the c-wave was measured by ERG (A) and then the amplitude of the b-wave was quantified (B), and the c-/b-wave ratio (C) was also estimated. The bars represent averages of the c-/b-wave ratio+/−the standard error (WT control n=5, rest of the groups n=10). The normality of the data was confirmed by the Kolmogorov-Smirnov test (P=0.43); to determine differences in the means of the groups, one-way ANOVA (P<0.05) and post hoc LSD tests were performed. *P<0.01 KI control vs KI 2.

FIG. 14. Optomotor test showing the visual acuity curve in normal mice (WT control), untreated Prpf31$^{A216P/+}$ mice (KI control), and Prpf31$^{A216P/+}$ mice treated with eye drops administered daily for two and a half months containing 2 mM resveratrol (KI RES) or 2 mM compound 2 diluted in a 13% hydroxypropyl-beta-cyclodextrin vehicle in PBS (KI 2) or only with the 13% hydroxypropyl-beta-cyclodextrin vehicle in PBS (KI CYCLE). Both WT and KI mice that did not receive any treatment (WT control and KI control) were used as controls. All the groups were subjected to 5,000 lux for 3 h and the evaluations were made 15 days after inducing light damage, the eye drops having been continued during this 2-week period. The optomotor test data were quantified and are shown in the chart. Each point represents averages of the number of positive responses+/− the standard error (WT control n=5, rest of the groups n=10). The normality of the data was confirmed by the Kolmogorov-Smirnov test in all spatial frequencies except for 0.031 and 0.061. To determine differences in the means of the groups, two-way ANOVA was performed, correlating both the different frequencies and groups (P<0.001) and the post hoc LSD test. *P<0.05 KI control vs. KI RES or **<0.001 KI control vs KI 2.

EXAMPLES

The invention will be illustrated below by means of tests conducted by the inventors that demonstrate the effectiveness of the product of the invention.

Example 1. In Vitro Neuroprotection Assays

The SH-SY5Y neuroblastoma cell line was cultured in petri dishes pre-treated with collagen (100 μg/ml) with F12 medium supplemented with penicillin/streptomycin and 10% inactivated fetal bovine serum.

Cell viability assays with neurons were prepared in 96-well plates pre-treated with collagen by seeding 20,000 cells/well in a volume of 100 μl and incubating the cells for 24 h before the addition of the compounds. The compounds to be tested were dissolved in DMSO and added in three different concentrations (1, 10 and 100 μM) in order to determine their toxicity. The final percentage of DMSO in each well was adjusted to 1%. The cell viability was evaluated 24 h after the addition of the compounds by means of the MTT assay according to the manufacturer's method. Mean values and standard deviations were calculated from at least 8 different measurements from several independent experiments.

Neuroprotection assays. The neurons were cultured and seeded in the same manner as for the cell viability assay. The compounds to be tested were dissolved in DMSO and added to three different concentrations (1, 10 and 100 μM) and, after 10-minute incubation, hydrogen peroxide (100 μM) was added to the medium. The final percentage of DMSO in each well was adjusted to 1%. The cell viability was evaluated 24 h after the addition of the compounds by means of the MTT assay according to the manufacturer's method. Mean values and standard deviations were calculated from at least 8 different measurements from several independent experiments. Neuronal recovery was calculated by normalizing the results of the neuronal viability experiments after the addition of our compounds and $H_2O_2$ to the positive control of each experiment (neurons+$H_2O_2$).

Figure 1:
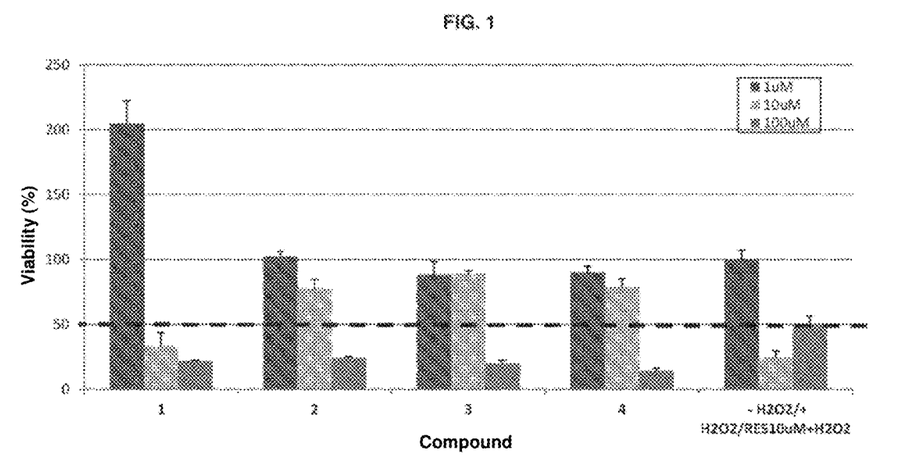
FIG. 1. Cell viability in neuroblastoma SH-SY5Y after damage with $H_2O_2$ and treatment with the different compounds 1-4. The controls are —$H_2O_2$=1% DMSO solution; +$H_2O_2$=$H_2O_2$ in 1% DMSO; RES 10 μM+$H_2O_2$=resveratrol 10 μM in $H_2O_2$ in 1% DMSO.

It is observed that the RES 10 μM control recovers up to 50% of cell viability (indicated by the arrow in FIG. 1). In contrast, acylated piceid derivatives (1, 2, 3 and 4) recover between 70 and 200% of viability at concentrations between 1 and 10 μM. All of those at 100 μM appear to exhibit toxicity.

Example 2. In Vitro Inflammation Assays

RAW 264.7 macrophages were cultured in P75 with high-glucose DMEm supplemented with penicillin/streptomycin and 10% inactivated fetal bovine serum.

The cell viability assays with RAW macrophages were prepared in 96-well plates by seeding 25,000 cells/well in a volume of 100 μl and incubating the cells for 4 h before the addition of the compounds. The compounds to be tested were dissolved in DMSO and added in three different concentrations (1, 10 and 100 μM) in order to determine their toxicity. The final percentage of DMSO in each well was adjusted to 1%. The cell viability was evaluated 24 h after the addition of the compounds by means of the MTT assay according to the manufacturer's method. Mean values and standard deviations were calculated from at least 8 different measurements from several independent experiments.

Testing of mitigation of damage caused by the addition of LPS. The RAW 264.7 macrophages were cultured according to the procedure described above. The compounds to be tested were dissolved in DMSO and added to three different concentrations (1, 10 and 100 µM) and, after 10-minute incubation, LPS (100 ng/ml) was added to the medium. The final percentage of DMSO in each well was adjusted to 1%. The cell viability was evaluated 24 h after the addition of the compounds by means of the MTT assay according to the manufacturer's method. Mean values and standard deviations were calculated from at least 8 different measurements from several independent experiments.

Figure 2:
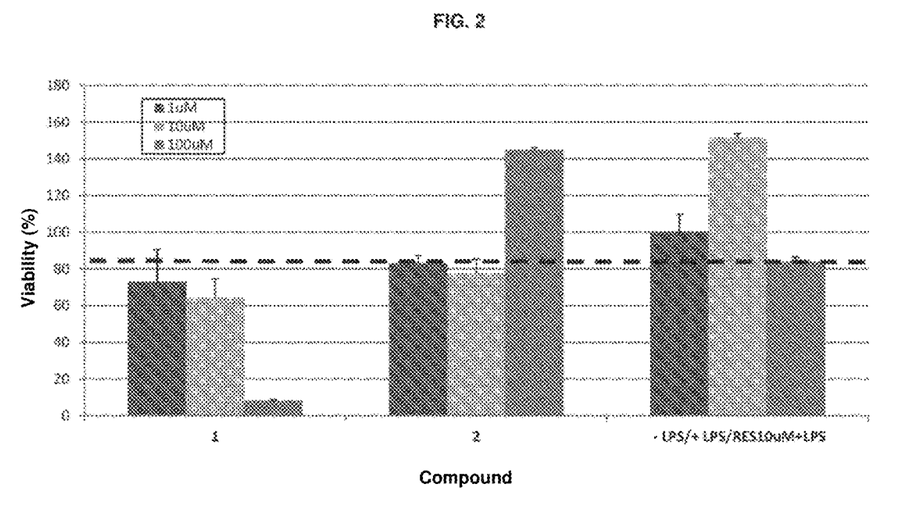
FIG. 2. Cell viability in RAW macrophages after inflammation produced with LPS and treatment with the different compounds 1-2. The controls are –LPS=1% DMSO solution; +LPS=1% DMSO solution with LPS; RES 10 μM+LPS=resveratrol 10 μM in 1% DMSO solution with LPS.

It is observed that the RES 10 µM control recovers up to 82% of cell viability (indicated by the arrow in FIG. 2). Compound 2 recovers between 80 and 140% of viability at concentrations between 1 and 100 µM.

Example 3. Measurements of Inflammation Parameters (Cytokines) in Assay with LPS To determine the production of cytokines, $5 \times 10^5$ RAW 264.7 macrophages were seeded in 24-well plates (0.5 ml per well). The compounds to be tested were then added (10 µM), and the macrophages were either stimulated or not through the addition of LPS (1 µg/ml) to the culture medium. After 24 hours, the levels of IL-6 and TNF-α were measured in the supernatants by ELISA using the capture and biotinylated antibodies from BD PharMingen and PrepoTech (Gonzalez-Rey et al., Gut. 2009; 58:929-939; Sánchez et al., Stem Cells. 2011; 29:251-262). The levels of NO in the supernatants at 24 hours were measured indirectly by determining the nitrite concentration in the medium using the Griess reagent (Anderson et al., Gut. 2013; 62:1131-1141). A minimum of two independent experiments and three replicates per experiment were performed for each measured value. The values are expressed as the mean±standard deviation.

Figure 3:
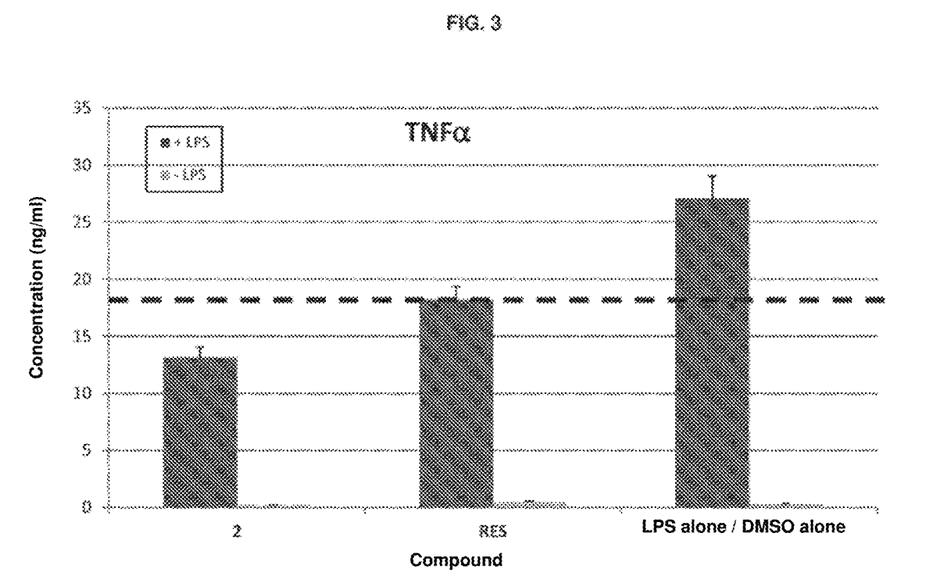
FIG. 3. Concentration of TNF-alpha in culture medium after inflammation by LPS in RAW macrophages and treatment with compound 2 and RES control. The controls are LPS alone=1% DMSO solution with LPS; DMSO only=1% DMSO solution.
Figure 4:
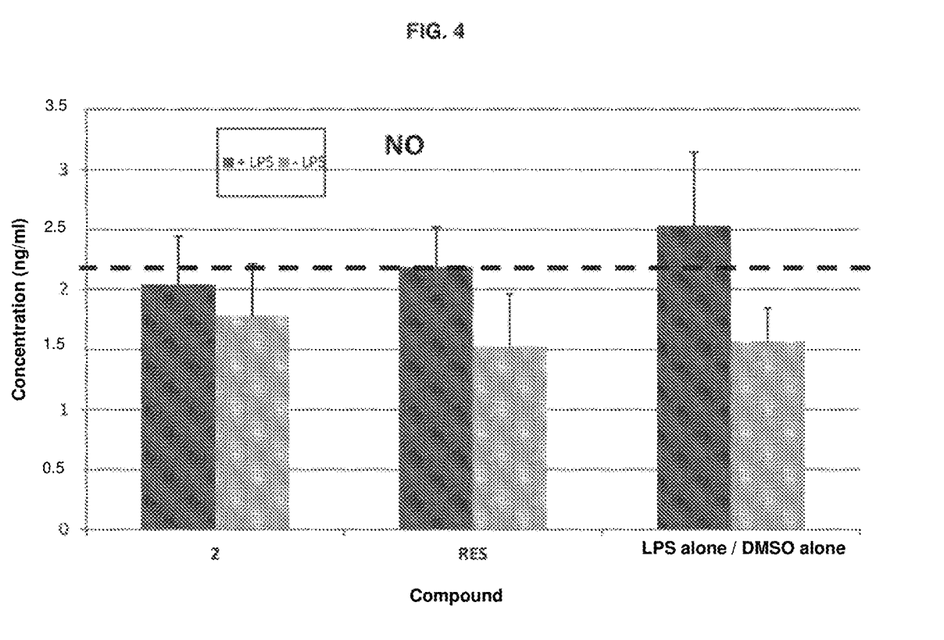
FIG. 4. Concentration of NO in culture medium after inflammation by LPS in RAW macrophages and treatment with compound 2 and RES control. The controls are LPS alone=1% DMSO solution with LPS; DMSO only=1% DMSO solution.
Figure 5:
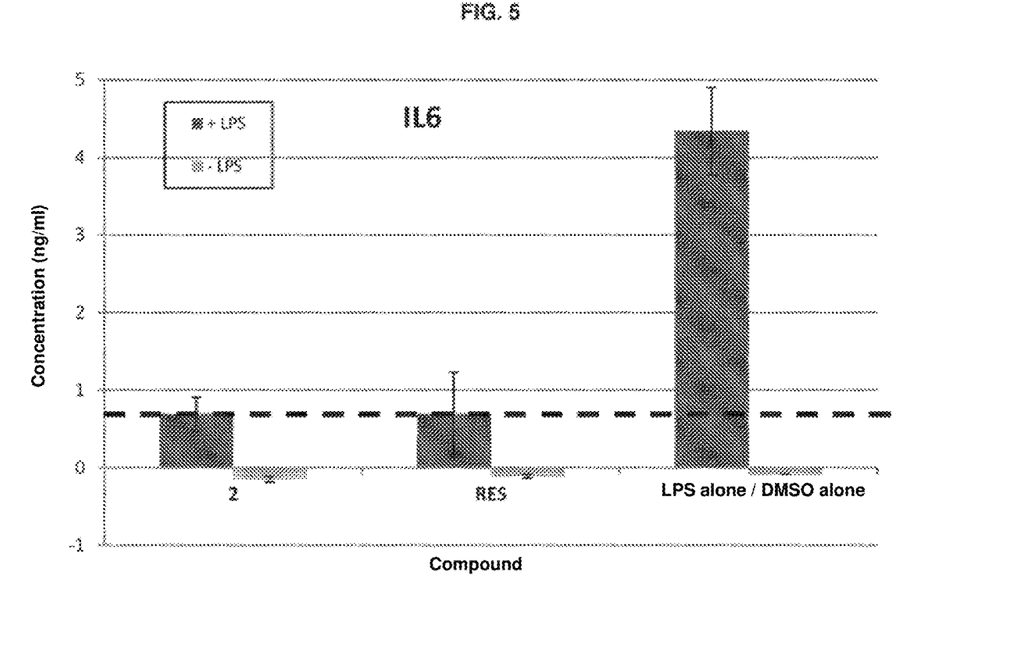
FIG. 5. Concentration of IL6 in culture medium after inflammation by LPS in RAW macrophages and treatment with compound 2 and RES control. The controls are LPS alone=1% DMSO solution with LPS; DMSO only=1% DMSO solution.

In the previous assay, the levels of various inflammation parameters were measured (TNF-α, NO, and IL-6) by ELISA after treatment with RES or with compound 2 (FIGS. 3, 4, and 5).

It is observed that the control of RES 10 µM significantly decreases inflammatory parameters (TNF-α, NO, and IL-6) (indicated by the bar in bold). Compound 2 decreases TNF-α and NOT even more than RES and similarly to IL-6.

Example 4. Evaluation of the Neuroprotective Capacity of Various Silylated Compounds in a Model of Neurodegeneration in Zebrafish Larvae Induced by Pentylenetetrazole (PTZ)

The objective of this assay was to analyze the protective effect of compound 2 and of the resveratrol (RES) control in a model of neurotoxicity induced by the neurotoxin pentylenetetrazole (PTZ). As an experimental model, the zebrafish larva (Danio rerio) was used to study the effect of the compounds on acetylcholinesterase activity (AChE) in larvae at 5 days post-fertilization (dpf).

Studies of the central nervous system (CNS) in zebrafish (Kimmel et al., Dev Dyn, 1995 July; 203(3):253-310), show that, at 24 hours of development, the brain of the embryo has already segmented and some structures such as the neural tube, the notochord and the somites (muscle, and bone precursors). At 5 days post-fertilization (5 dpf), the animal has formed sensory organs such as eyes and otoliths. In addition, the heart, liver, kidneys, and pancreas, as well as the circulatory, digestive, and nervous systems are fully functional. At this time, the animal is able to respond to visual, olfactory, and mechanical stimuli and begins the search for food.

AChE is an enzyme that degrades through its hydrolytic activity the neurotransmitter acetylcholine in choline and an acetate group. It is found chiefly in neuromuscular junctions and in the cholinergic nervous system, where its activity has the function of ending synaptic transmission (Behra et al., Nat Neurosci. 2002 February; 5(2): 111-8.). Acetylcholine is a neurotransmitter involved in the control of movement and is an important modulator of cognitive functions such as learning and memory (Hasselmo et al., Neuropsychopharmacology. 2011 January; 36(1): 52-73). Adequate levels of acetylcholinesterase thus reflect a healthy neuronal state.

Zebrafish embryos were seeded in 50 ml of dilution water (AD) in a Petri dish and grown to 5 dpf (larval stage). Only those larvae that did not exhibit any type of external anomaly were used to perform the assay. Next, the larvae were transferred using a Pasteur pipette to a 24-well microplate, so that each well contained five larvae, making ten replicates per condition. First, the pre-treatment of the 5 dpf larvae was performed. For this, the larvae were incubated at 26±1° C. for 1 hour in a volume of 2 ml of AD for the two control groups (Control and Control+PTZ), of physostigmine (Phys) 20 µM, which is a commercial inhibitor of the enzyme AChE for the Phys group, and of the test compounds at a concentration of 10 µM. A medium exchange was then carried out, and the larvae were incubated with the compounds in combination with 5 mM PTZ for 6 hours at 26±1° C. After this incubation period, all of the larvae were examined, and it was determined that the general state of the larvae was totally normal, without any visible anomaly or anomalous behavior. Finally, the larvae were processed for the analysis of the AChE activity.

Determination of AChE levels. Once the experimental period was completed, larvae processing was carried out for the determination of AChE according to the technical study protocol (Measurement of acetylcholinesterase activity (AChE) in cell cultures and zebrafish larvae). The larvae were homogenized mechanically, and the samples were centrifuged to obtain the supernatant, which were used to determine the levels of the AChE enzyme as a function of the treatments administered. In addition, the determination of total protein of each experimental group was carried out according to the technical study protocol (Quantification of protein by BCA, as a normalization process). Finally, the AChE levels determined in the control group were taken as a reference measurement and deemed to be 100%.

Figure 6:
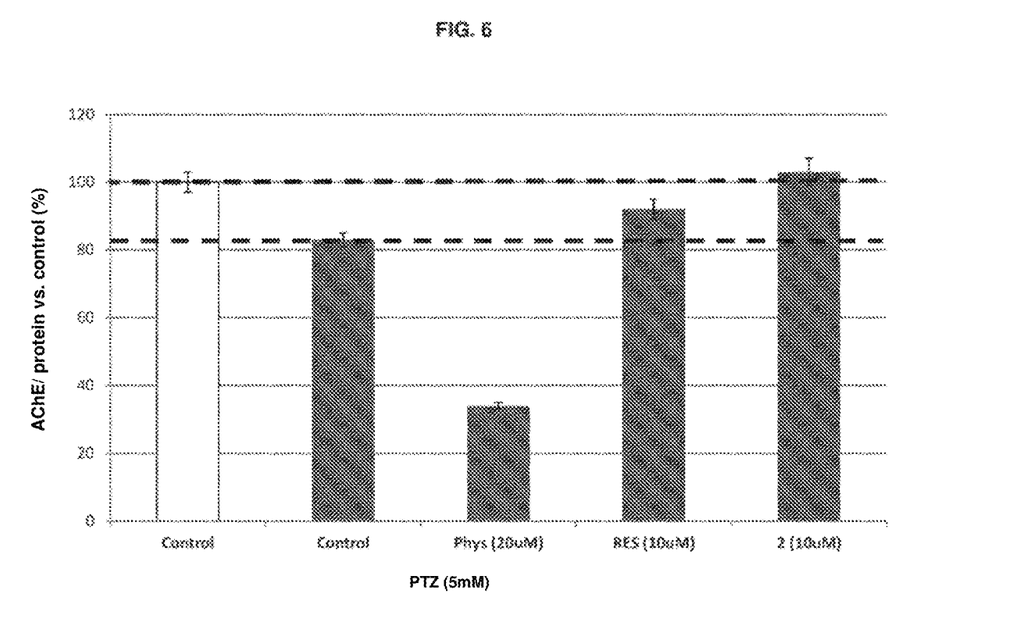
FIG. 6. AChE activity with respect to the control of compound 2 and the RES control.

Compound 2 significantly prevents the decrease in AChE activity induced by PTZ in the 5dpf larvae, showing a clear neuroprotective effect that is greater than that observed for RES (see FIG. 6).

Example 5.—Toxicity Assay in Zebrafish

Twenty zebrafish embryos were incubated for each concentration of compound to be tested (1 to 4). The concentrations used of each compound are 0.1 µM, 1 µM, 10 µM, 100 µM and 1 mM. The incubation period goes from 0 to 96 hours post fertilization (hpf). A negative control of 1%

DMSO and a positive control of N, N-diethylaminobenzaldehyde (DEAB) are included. After the incubation period, the LC50 (lethal dose for 50% of the animals) is calculated.

The zebrafish embryo toxicity assay was carried out for compound 2 and the resveratrol (RES) control, and both exhibited acceptable toxicity (LC50<140 uM) and (LC50<1000 uM), respectively.

Example 6. Assays in Rd10 Mice, Retinal Degeneration Model

Figure 7:
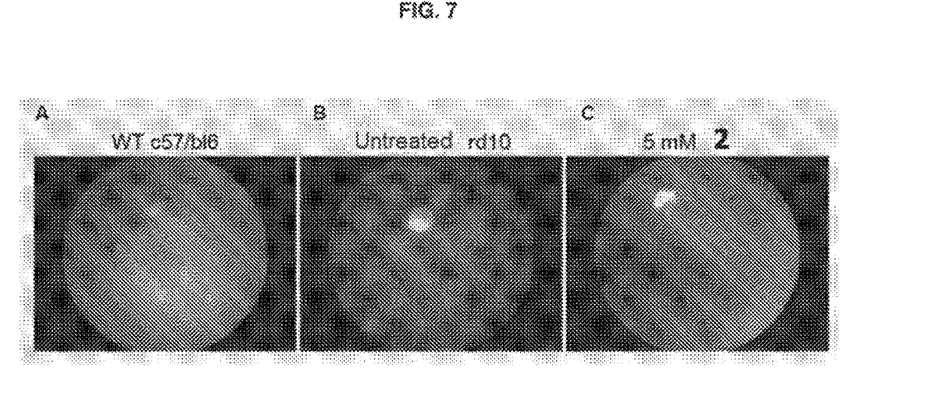
FIG. 7. Fundus of normal c57/bl6 mouse (WT) (A), untreated rd10 mouse (B), and injected with 5 mM of compound 2 (C) at 15 days after subretinal administration of the compounds. The absence of pigment in the fundus of the mouse treated with compound 2 is observed.
Figure 8:
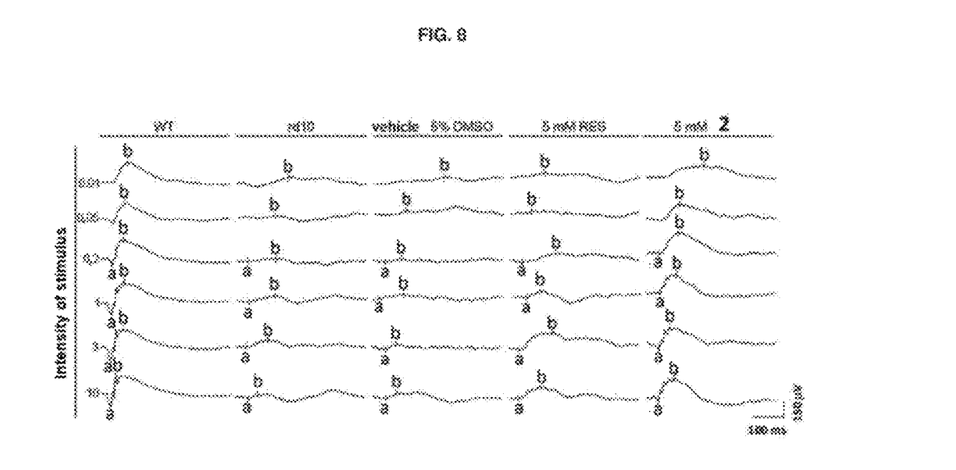
FIG. 8. Electroretinogram of normal c57/bl6 mouse (WT), untreated rd10 mouse, DMSO vehicle 5%, 5 mM resveratrol (RES) and 5 mM compound 2 at 15 days after subretinal injection. The amplitude of the a- and b-waves was preserved in the group treated with compound 2 in a greater proportion than in the rd10 mice that were untreated or treated with RES or with 5% DMSO vehicle.
Figure 9:
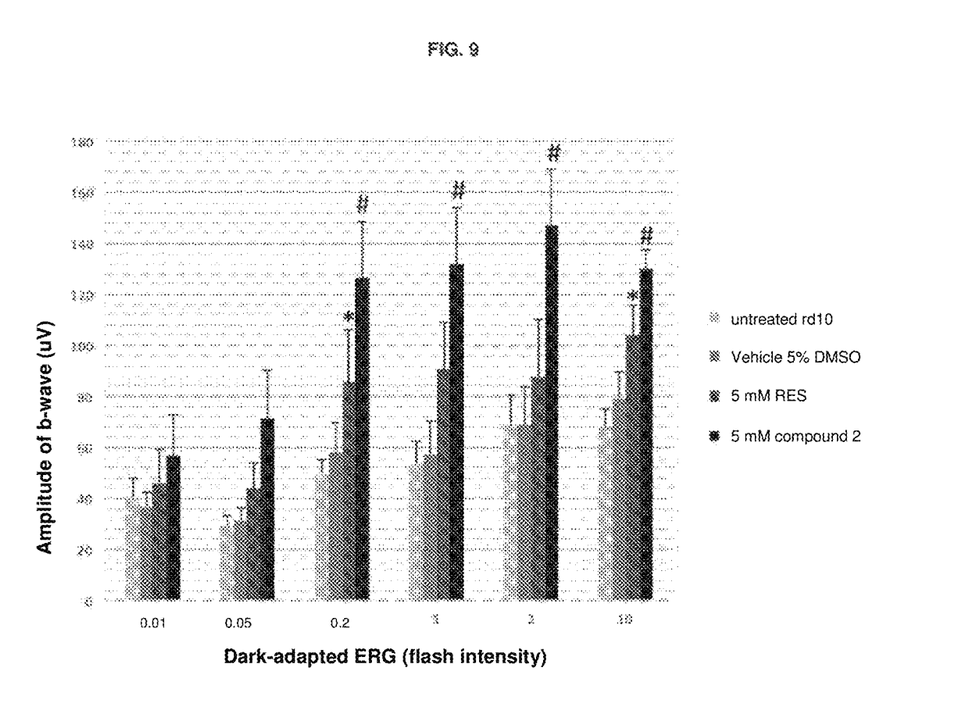
FIG. 9. Amplitude of the b-wave in untreated rd10 mice, rd10 mice treated with 5% DMSO vehicle, with 5 mM RES, and with 5 mM compound 2 at 15 days after administration of the subretinal injections. Each bar represents the average of the b-wave in 6 mice per group±the standard error of the mean. The amplitude of the b-wave was significantly increased in the mice treated with compound 2 in the dark-adapted ERG with flash intensities of 0.2, 1, 3 and 10 cd xs/$m^2$. The statistical analysis was performed by one-way ANOVA with post hoc DMS test *$p<0.05$; #$p<0.01$.
Figure 10:
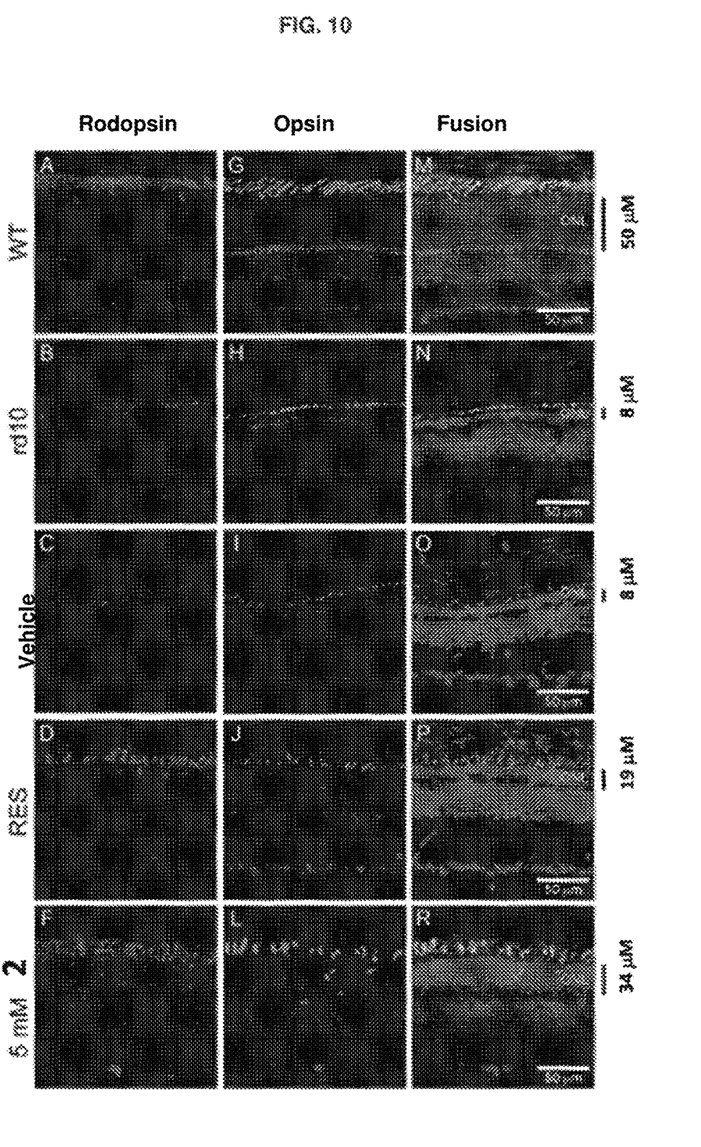
FIG. 10. Immunofluorescence of normal c57/bl6 mouse (WT) (A, G, M), untreated rd10 mouse (B, H, N), or rd10 mice treated with vehicle (C, I, O), with 5 mM RES (D, J, P) and with 5 mM compound 2 (F, L, R) at 15 days after administration of the subretinal injections. The sections of the retina were immunostained with anti-rhodopsin antibodies (red) to label the rods and anti-opsin (green) to label the cones. The nuclei were stained with DAPI. In all of the groups that were treated with SIRT1 activators, more labeling of rhodopsin and opsin was observed than in the untreated group, but the signal of this immunolabeling was more intense in the group treated with compound 2. Likewise, the thickness of the outer nuclear layer (ONL) was greater than in the group treated with RES.

The rd10 mouse is a model of retinitis pigmentosa due to a mutation in the Pde6b gene that results in the degeneration of the photoreceptors that begins on postnatal day 15-16 (P15-16) and is completed within one month (P30). In this model, the degeneration begins in the rods and then continues with cones and finally the retinal pigment epithelium (RPE). The degeneration in this model occurs as a consequence of the loss of the function of Pde6b, which ultimately leads to a continuous entry of $Ca^{++}$ in the cones with a significant production of reactive oxygen species (ROS), infiltration of macrophages, and activation of pro-apoptotic proteins. At the histological level, a loss of nuclei is observed in the outer nuclear layer of the retina (the layer in which photoreceptor nuclei are located), as well as the loss of the specific markers of rods (rhodopsin) and cones (opsin). The electroretinogram (ERG), which measures the electrical response of the retina to visual stimuli, is markedly affected in rd10 mice, with progressive loss of the amplitude of the a- and b-waves of the ERG. Finally, the fundus used to evaluate the macroscopic morphology of the bottom of the eye exhibits changes at one month of age in the rd10 mice, with accumulation of dark pigments in the periphery due to the degeneration of the RPE. To evaluate the protective effect of our compounds on the retina, we first used the rd10 model. Rd10 homozygous mice were injected in the subretinal space at P13 (two to three days before the onset of degeneration) with 1 µl of vehicle (5% DMSO in PBS) or resveratrol RES (5 mM), as well as compound 2 (5 mM). Then, 15 days after having been injected, fundus, ERG, and histological changes were evaluated in the untreated mice, those treated with the vehicle, and those treated with RES and compound 2. Evaluation of the fundus revealed a lower amount of pigment accumulation in the retinas of mice treated with compound 2 compared to the untreated mice (FIG. 7). The ERG in the treated mice was also evaluated 15 days after the injections. The amplitude of the a- and b-waves in the ERGs were quantified, and the statistical analysis was performed using two-way ANOVA and post hoc DMS. A value of $p<0.05$ was considered significant. The b-wave amplitude in the ERG of dark-adapted mice (flash intensities of 0.2, 1, 3, and 10×cd $s/m^2$) underwent a significant increase in the group of mice treated with compound 2 compared to the controls (FIGS. 8 and 9). Finally, the immunofluorescence study was performed in order to observe the presence of markers of rods (rhodopsin) and cones (opsin) (FIG. 10). The number of photoreceptor nuclei present in the outer nuclear layer (ONL), as well as the immunostaining of rhodopsin, was much greater in rd10 mice treated with compound 2 than in those treated with RES and in the controls.

Example 7.—Assays on Prpf31 Mice, RPE Retinal Degeneration Model)

Prpf31$^{A216P/+}$ mice are a useful model for assessing the degeneration of the RPE. This model is characterized by an increase in the thickness of the Bruch membrane and accumulation of esterified cholesterol between said membrane and the RPE produced by a defect in the splicing of the mRNA of relevant genes of the visual cycle, such as RPE65 and RDH12. The accumulation of toxic products derived from retinol leads to an increase in ROS, infiltration of macrophages, and primary degeneration of the RPE. The degeneration of the RPE occurs late, at approximately 8 months of age. The phenotypic characteristics of this model can be exacerbated by exposure to intense light and are characterized primarily by accumulation of pseudo-drusenoid lesions and regions of atrophy observed in the fundus, with a loss of visual acuity and perception of contrast being observed, as well as a decrease in the amplitude of the c-wave of the ERG and a decrease in the thickness of the retina.

To evaluate the protective effect of the administration of our compounds in eye drops, we used heterozygous 6 month-old Prpf31$^{A216P/+}$ (KI) mice that were treated topically with 20 µl of the studied compounds applied directly on the corneal surface daily (L-V) for two and a half months. The compounds used were RES and compound 2, which were diluted in a solution of 13% hydroxypropyl-beta-cyclodextrin (CYCLO) in order to obtain a final concentration of 2 mM of each compound. After two and a half months of application of the eye drops with CICLO, RES, or compound 2, the mutant KI mice were exposed to a light source of 5,000 lux for 3 hours. Normal (WT) and KI mice were also exposed to intense light as test control without receiving any treatment. Subsequently, the fundus of the animals was evaluated, in addition to the visual acuity by means of the optomotor test, the thickness of the retina by means of optical coherence tomography (OCT), and the amplitude of the c-wave by ERG.

Figure 11:
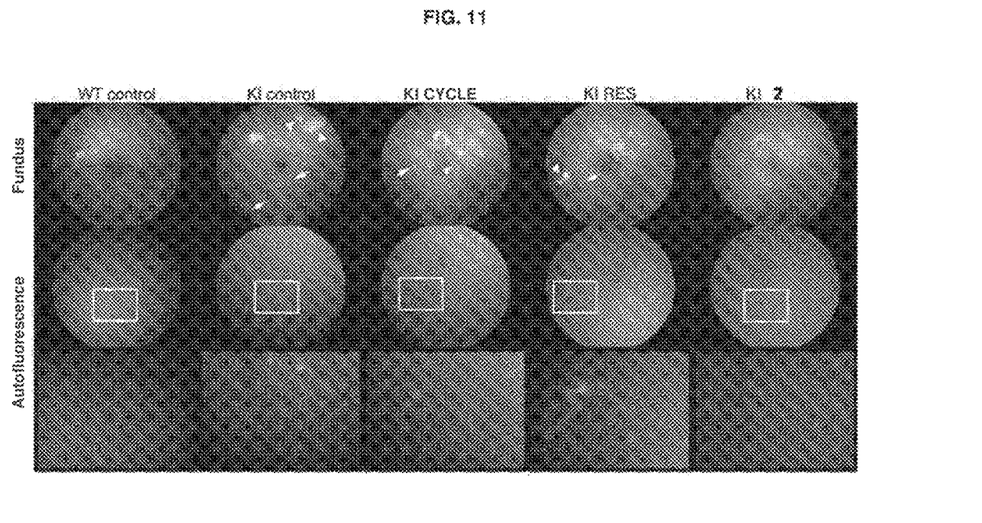

Evaluation of the Fundus:

Two categories were used to quantify the macroscopic characteristics of the fundus: abnormal and normal fundus. The fundi categorized as abnormal were those in which the presence of autofluorescent pseudo-drusenoid lesions was observed (FIG. 11; arrows) or with regions of focal atrophy (FIG. 11; arrowheads). The percentage of abnormal fundi in the WT mice exposed to light (WT control) was 20%, and in the untreated KI (KI control) it was 90%. Meanwhile, this percentage was reduced to 30% in mice treated with compound 2 (KI 2) and only to 60% in both mice treated with CYCLE (KI CYCLE) and RES (KI RES) (table 1). When performing the statistical analysis for each dichotomous variable, we observed that there is a statistically significant relationship between the presence of normal fundi and mice treated with compound 2 when compared with the control KI group (chi-square=7.5; P<0.01, Fisher's exact test P<0.05) and with a probability of obtaining a normal fundus in the group treated with compound 2 of seven times greater than in the control KI (normal RR=7, IC95%=1.044-46.949). These values were similar to those observed when comparing WT control and KI control (chi-square=7.35, P<0.01, Fisher's exact test P<0.05) and with a probability of obtaining a normal fundus in the WT control group of eight times greater than in the control KI (normal RR=8; IC95%=1.184-54.043). In both the group treated with CICLO and that treated with RES, no statistically significant association was observed when comparing each one to the control KI group. The conclusion of this experiment is that treatment with compound 2 prevented the formation of autofluorescent pseudo-drusenoid lesions and regions of focal atrophy in the Prpf31$^{A216P/+}$ mouse.

TABLE 1

Quantification of the number of abnormal and normal fundi in WT and Prpf31$^{A216/+}$ (KI) mice without treatment or when treated with 13% CYCLE, RES, and compound 2.

| Groups | Fundus | | |
|---|---|---|---|
| | Abnormal (%) | Normal (%) | Total |
| WT control | 1 (20) | 4 (80)# | 5 |
| KI control | 9 (90) | 1 (10) | 10 |
| KI CYCLE | 6 (60) | 4 (40) | 10 |
| KI RES | 6 (60) | 4 (40) | 10 |
| KI 2 | 3 (30) | 7 (70)* | 10 |
| Total (%) | 25 (55.6) | 20 (44.4) | 45 |

*KI 2 vs. KI control (chi-square = 7.5; P < 0.01; Fisher's exact test P < 0.05; RR normal = 7; IC95% = 1.044-46.949).
WT control vs KI control (chi-square = 7.35, P < 0.01, Fisher's exact test P < 0.05, normal RR = 8, 95% CI = 1.184-54.043).

Figure 12:
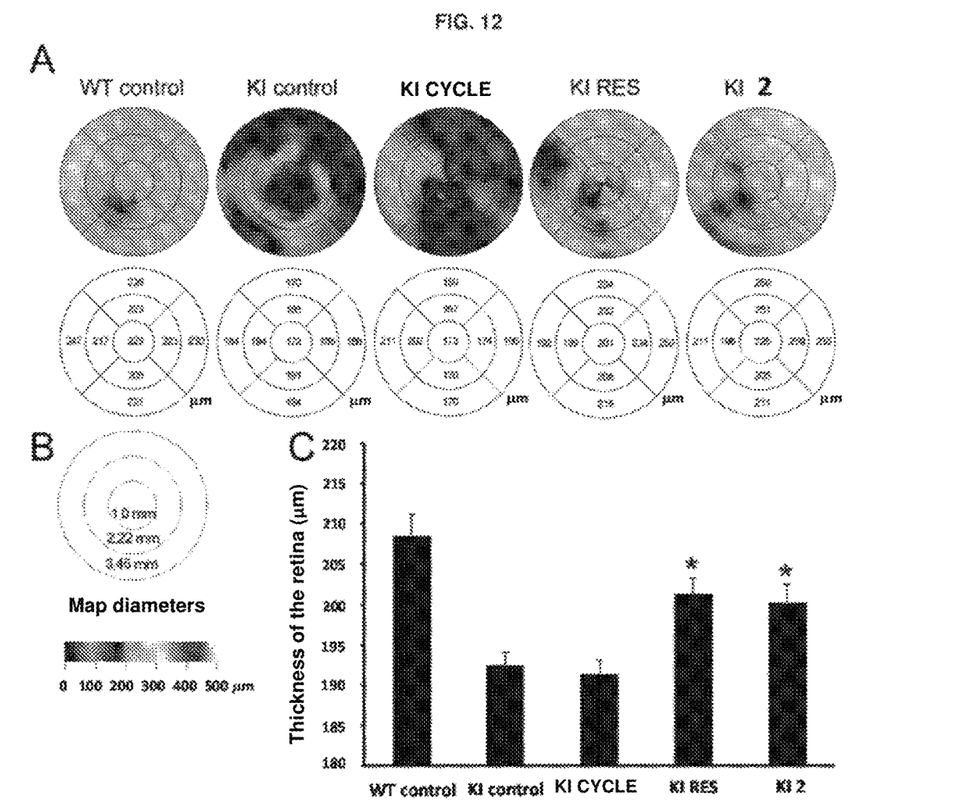

Thickness of the Retina:

To evaluate the thickness of the retina in vivo, a Stratus OCT (Zeiss) was used with a scanner adjusted to 6 lines of 3.45 mm each arranged radially. Six measurements were performed in each eye, upon which the retinal map was prepared (FIG. 12) with the thickness of the retina quantified from the ganglion cell layer to the RPE. The thickness of the retina was significantly greater in the groups treated with RES and compound 2 when compared to the control KI group (FIG. 12; C); these results show that treatment with SIRT1 activators prevented the production of retinal atrophy in KI mice after exposure to an intense light source.

Figure 13:
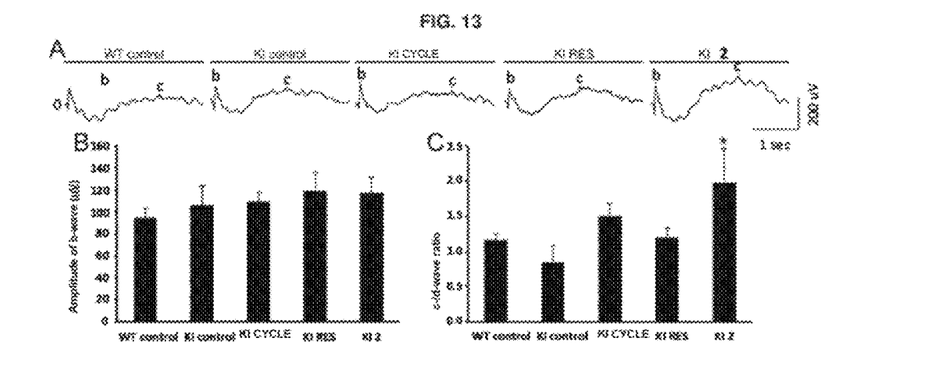

Evaluation of the Function of the RPE:

To evaluate the functional integrity of the RPE, the amplitude of the c-wave in the ERG was measured. The c-wave is defined as a positive slow wave that appears after the b-wave and is used to measure the functional integrity of the RPE. Since the amplitude of this wave can be affected by the integrity of the photoreceptors, it is best to normalize the results with the amplitude of the b-wave, for which reason a quantification was performed of the proportion of the amplitude of the c-wave between the amplitude of the b-wave (c-/b-wave ratio) (FIG. 13). The c-/b-wave ratio was significantly higher in the group treated with compound 2, which suggests that the functional integrity of the RPE was maintained in this group.

Figure 14:
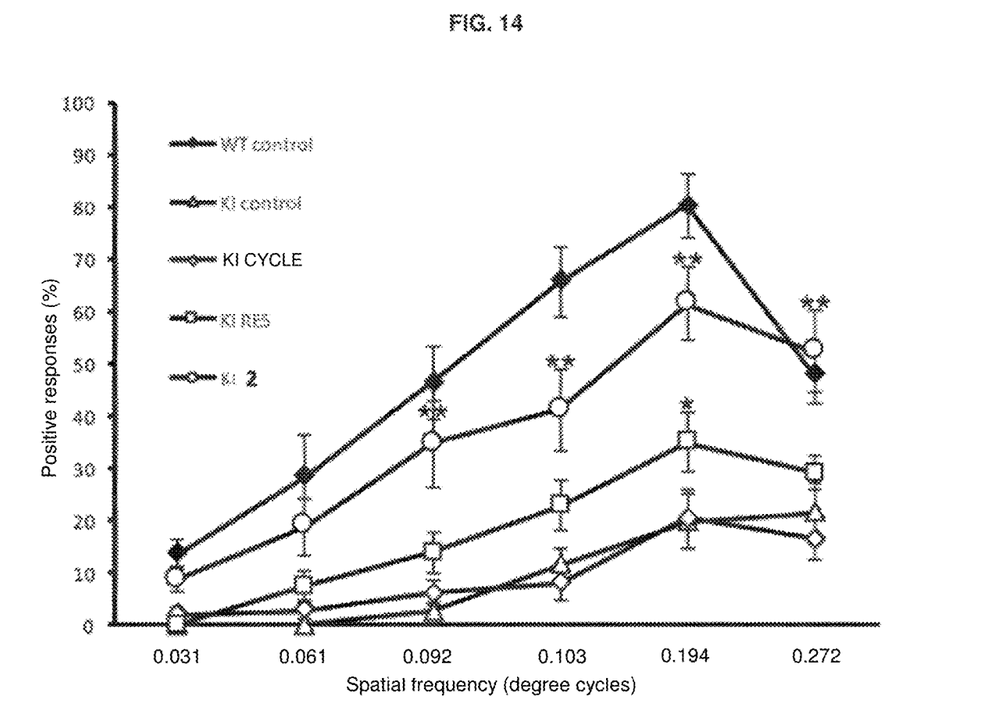

Visual Acuity:

Finally, the optomotor test was performed in order to assess visual acuity; this test consists in evaluating the optokinetic visual follow-up reflex that is stimulated by the rotating movement of different black and white serial horizontal bars. The response to said visual stimulus is manifested by a cervical tracking movement in the same direction of the rotation as the bars. Cervical movement is recorded with a camera, and the spatial frequency of the bars varies randomly, as does the direction of rotation of the bars. The optomotor test was evaluated at 6 different spatial frequencies (0.031, 0.061, 0.092, 0.103, 0.194, and 0.272 cycles/degree), and the spatial vision was measured by the number of positive responses. In the group treated with compound 2, the number of positive responses was significantly higher than in control KI groups in the majority of frequencies studied (0.092, 0.103, 0.194, and 0.272 cycles/degree), and KI RES was only significant at 0.194 cycles/degree (FIG. 14).

In conclusion, in the experiments described in examples 6 and 7, we have demonstrated that the SIRT1 activator (compound 2) has a protective effect on the retina of rd10 and Prpf31$^{A216P/+}$ mice. This retinoprotective effect suggests that this molecule could potentially be useful for the treatment of RP and other degenerative pathologies of the retina and RPE in which ROS, inflammation, and apoptosis occur, such as in AMD.

What is claimed is:

1. A method of preventing retinal degeneration and/or treating ocular pathologies, wherein the method comprises administering to a patient in need of such treatment a therapeutically effective amount of trans-resveratrol-3-O-(6'-O-octanoyl)-β-D-glucopyranoside
    or any of its isomers, their pharmaceutically acceptable salts, esters, tautomers, polymorphs, or hydrates
    wherein the pathologies are hereditary degenerative pathologies of a retina selected from retinitis pigmentosa and pathologies within the group of retinal dystrophies selected from the group consisting of autosomal dominant retinitis pigmentosa, autosomal recessive retinitis pigmentosa, retinitis pigmentosa linked to the X chromosome, sporadic retinitis pigmentosa, retinitis pigmentosa associated with other syndromes, Cokayne syndrome, cone dystrophies, cone and rod degeneration, Leber's congenital amaurosis, retinitis punctata albescens, choroideremia, choroidal and retinal gyrate atrophy, choroidal generalized dystrophy, juvenile retinoschisis, Wagner's vitreoretinal degeneration, autosomal dominant vitreoretinal choroidopathy, fundus albipunctatus, Stargardt's disease, Best vitelliform macular dystrophy, Usher syndrome, Bardet-Biedl syndrome, fenestrated macular dystrophy, Sorsby pseudoinflammatory macular dystrophy, and dominant drusen;
    wherein the ocular pathologies are age-related macular degeneration;
    wherein the ocular pathologies are degenerative inflammatory pathologies of the retina and of the optic nerve;
    wherein the ocular pathologies are ocular pathologies that increase intraocular pressure and that involve degeneration of the ganglion cells of the retina and atrophy of the optic nerve selected from the group consisting of open-angle and closed-angle glaucoma;
    wherein the ocular pathologies are neurological pathologies that are accompanied by degenerative lesions of the retinal or optic nerve selected from the group consisting of amyotrophic lateral sclerosis, multiple sclerosis, Parkinson's disease, Alzheimer's disease, Graefe syndrome, Hallgren syndrome, Hallen Vorden Spatz syndrome, autosomal dominant cerebellar ataxia, and pigmentary degeneration of the retina.

2. The method of claim 1, wherein the compound is administered together with a controlled-release system.

3. The method of claim 2, wherein the controlled-release system is a cyclodextrin.

4. The method of claim 3, wherein the cyclodextrin is 2-hydroxypropyl β-cyclodextrin.

5. The method of claim 1, wherein the degenerative inflammatory pathology of the retina and of the optic nerve is diabetic retinopathy.

6. The method of claim 1, wherein the ocular pathologies are retinitis pigmentosa and age-related macular degeneration.

* * * * *

UNITED STATES PATENT AND TRADEMARK OFFICE
CERTIFICATE OF CORRECTION

PATENT NO. : 11,213,536 B2
APPLICATION NO. : 16/463786
DATED : January 4, 2022
INVENTOR(S) : Juan Carlos Morales Sanchez It is certified that error appears in the above-identified patent and that said Letters Patent is hereby corrected as shown below:

In the Drawings

Sheet 6 of 9 (FIG. 10), Line 1, delete "Rodopsin" and insert -- Rhodopsin --.

In the Specification

Column 5, Line 32, delete "Hallen Vorden" and insert -- Hallervorden --.

Column 9, Line 35, delete "PrepoTech" and insert -- PeproTech --.

Column 10, Line 57, delete "5dpf" and insert -- 5 dpf --.

In the Claims

Column 14, Line 49, Claim 1, delete "Hallen Vorden" and insert -- Hallervorden --.

Signed and Sealed this
Twenty-second Day of November, 2022

Katherine Kelly Vidal
*Director of the United States Patent and Trademark Office*